US010286418B2

(12) United States Patent
Watanabe

(10) Patent No.: US 10,286,418 B2
(45) Date of Patent: May 14, 2019

(54) NEBULIZER

(71) Applicant: L'OREAL, Paris (FR)

(72) Inventor: Yuichi Watanabe, Hiratsuka (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/306,782

(22) PCT Filed: Apr. 28, 2015

(86) PCT No.: PCT/JP2015/063402

§ 371 (c)(1),
(2) Date: Oct. 26, 2016

(87) PCT Pub. No.: WO2015/167018

PCT Pub. Date: Nov. 5, 2015

(65) Prior Publication Data

US 2017/0050203 A1 Feb. 23, 2017

(30) Foreign Application Priority Data

May 1, 2014 (JP) ................................ 2014-094673

(51) Int. Cl.
*A45D 34/02* (2006.01)
*A61M 35/00* (2006.01)
(Continued)

(52) U.S. Cl.
CPC .............. *B05B 15/50* (2018.02); *A45D 34/02* (2013.01); *A61M 35/00* (2013.01); *B05B 17/0646* (2013.01)

(58) Field of Classification Search
CPC ..... B05B 15/02; B05B 17/06; B05B 17/0607; B05B 17/063; B05B 17/0638; B05B 17/0646; B05B 17/0653; A61M 35/00
See application file for complete search history.

(56) References Cited

U.S. PATENT DOCUMENTS 4,246,076 A * 1/1981 Gardner .................. B41J 2/162 205/73
5,823,428 A * 10/1998 Humberstone ..... B05B 17/0646 239/102.2
(Continued)

FOREIGN PATENT DOCUMENTS

EP 2548665 A1 1/2013
JP 2003-136005 5/2003
(Continued)

OTHER PUBLICATIONS

International Search Report and Written Opinion for PCT/JP2015/063402, dated Jul. 21, 2015.
Office Action for JP 2014-094673 dated Sep. 4, 2017, 10 pages.

*Primary Examiner* — Darren W Gorman
(74) *Attorney, Agent, or Firm* — The Marbury Law Group, PLLC

(57) ABSTRACT

To provide a mist spraying device (1) capable of easily resolving clogging of micropores when they are clogged. The present invention provides a mist spraying device (1) including: a vibration plate (6) having an atomization part in which multiple micropores are formed; a vibration generator (10) for vibrating the vibration plate (6); and a supply part for supplying a liquid to the atomization part (8), the liquid supplied to the atomization part (8) being atomized by vibration of the vibration plate (6) and sprayed, wherein the mist spraying device further includes a heating element (12), and the heating element (12) serves to warm the atomization part.

14 Claims, 4 Drawing Sheets

(51) Int. Cl.
*B05B 15/50* (2018.01)
*B05B 17/00* (2006.01)

(56) References Cited

U.S. PATENT DOCUMENTS

| | | | | |
|---|---|---|---|---|
| 6,014,970 | A * | 1/2000 | Ivri .................. | A61M 15/0085 128/200.14 |
| 6,062,212 | A * | 5/2000 | Davison ........... | A61M 15/0085 128/200.14 |
| 2005/0082385 | A1 * | 4/2005 | Kuwada ............. | C23C 16/4405 239/128 |
| 2006/0255174 | A1 | 11/2006 | Ivri et al. | |
| 2008/0073447 | A1 | 3/2008 | Wang et al. | |
| 2009/0065600 | A1 * | 3/2009 | Tranchant ............. | A45D 34/02 239/4 |
| 2012/0143152 | A1 * | 6/2012 | Hunter ................. | A61B 5/0059 604/298 |
| 2013/0150812 | A1 | 6/2013 | Hunter et al. | |

FOREIGN PATENT DOCUMENTS

| | | |
|---|---|---|
| JP | 2010-023038 A | 2/2010 |
| JP | 2012-152467 | 8/2012 |
| JP | 2013-022199 | 2/2013 |
| JP | 2013-123681 | 6/2013 |
| JP | 2013-143933 | 7/2013 |
| JP | 2013-202498 | 10/2013 |
| JP | 2014-018765 | 2/2014 |

* cited by examiner

NEBULIZER

CROSS REFERENCE TO RELATED APPLICATIONS

This is a national stage application of PCT/JP2015/063402, filed internationally on Apr. 28, 2015, which claims priority to Japanese Application No. 2014-094673, filed on May 1, 2014, both of which are incorporated herein by reference in their entireties.

TECHNICAL FIELD

The present invention relates to a mist spraying device which atomizes a liquid contained in the device and sprays it continuously for a certain period of time.

BACKGROUND ART

An ultrasonic mist spraying device which atomizes and sprays a cosmetic liquid or pure water is now widely used. This mist spraying device atomizes a liquid contained in the device using a vibration generator. Such a device is capable of moisturizing the skin and cooling the skin in a non-contact manner.

Patent Literature 1 discloses a device which vibrates a vibration plate, in which multiple micropores are formed, by means of a piezoelectric vibrator to thereby atomize a liquid such as a beauty essence or water supplied into the micropores and spray the mist. Patent Literature 2 discloses a device which vibrates a vibration part by a piezoelectric element and atomizes a liquid attached to the vibration part.

This type of device is rarely used continuously for a long period of time, but is more often used for a short period of time, intermittently several times a day. This means that the device is likely to remain out of use for a prolonged time. Furthermore, the device can sometimes be out of use for a long period of time. In such cases, the cosmetic liquid remaining inside the micropores or the area surrounding them dries and becomes extremely viscous or crystallized. As a result, the micropores are clogged.

PRIOR ART DOCUMENT

Patent Document

[Patent Document 1] EP2548665

[Patent Document 2] Japanese Unexamined Patent Application, First Publication No. 2010-23038

SUMMARY OF INVENTION

Technical Problem

An object of the present invention is to provide a mist spraying device capable of easily resolving clogging of micropores.

Technical Solution

In order to solve the above problems, the present invention provides a mist spraying device including: a vibration plate having an atomization part in which multiple micropores are formed; a vibration generator for vibrating the vibration plate; and a supply part for supplying a liquid to the atomization part, the liquid supplied to the atomization part being atomized by vibration of the vibration plate and sprayed, wherein the mist spraying device further includes a heating element, and the heating element serves to warm the atomization part.

In the mist spraying device according to the present invention, the vibration generator may be arranged annularly around the atomization part, and the heating element may be arranged annularly around the atomization part.

In the mist spraying device according to the present invention, the vibration generator may be a piezoelectric element which generates vibration according to an input power, and the heating element may be a Peltier element.

In the mist spraying device according to the present invention, the micropores may have a tapered cross-section in an axial direction with the diameter on a mist jetting side being larger than the diameter on a liquid supply side. Alternatively, the micropores may have a stepped cross-section in the axial direction with the diameter on the mist jetting side being larger than the diameter on the liquid supply side. Moreover, the micropores may have an exponentially curved cross-section in the axial direction with the diameter on the mist jetting side being larger than the diameter on the liquid supply side. The liquid to be sprayed by the mist spraying device of the present invention may be a cosmetic liquid.

The present invention also provides a cosmetic kit including the mist spraying device and a cosmetic liquid. In one embodiment, the mist spraying device may include a tank and the cosmetic liquid may be contained in the tank. In another embodiment, the cosmetic liquid may be contained in a package which is mountable to the mist spraying device.

FIG. **4*a*** is a view showing a cross-section of a micropore which has a tapered cross-section in an axial direction.

FIG. **4*b*** is a view showing a cross-section of a micropore which has a stepped cross-section in the axial direction.

FIG. **4*c*** is a view showing a cross-section of a micropore which has an exponentially curved cross-section in the axial direction.

BEST MODE FOR CARRYING OUT THE INVENTION

Figure 1:
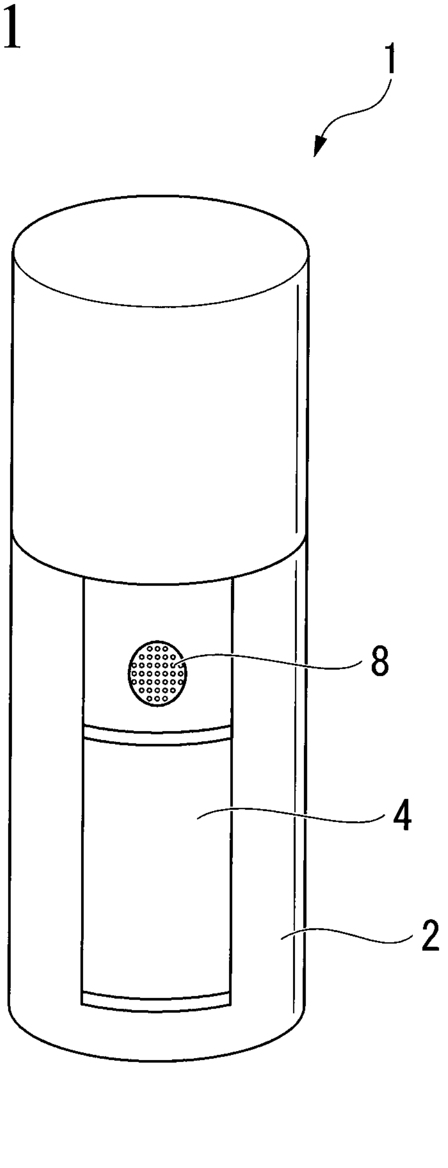
FIG. 1 is a view showing a mist spraying device equipped with a mist generation part according to an embodiment of the present invention.

In the following, an embodiment of the present invention will be described in detail with reference to the drawings. FIG. 1 is a view showing a mist spraying device 1 equipped with a mist generation part according to an embodiment of the present invention. The mist spraying device 1 can contain cosmetic liquid, and can atomize and spray this cosmetic liquid from an atomization part 8 continuously for a certain period of time, preferably less than 30 minutes, more preferably less than 10 minutes.

The mist spraying device 1 includes a substantially cylindrical housing 2. Inside the housing 2 are a tank (not shown) for containing the cosmetic liquid, a power source (not shown), and the mist generation part. The mist generation part includes: a vibration plate 6 in which the atomization part 8 for atomizing the cosmetic liquid is formed; a supply part (not shown) for supplying the cosmetic liquid to the atomization part 8; a vibration generator 10 for vibrating the vibration plate 6; and a heating element 12 for warming the atomization part 8.

The mist spraying device 1 further includes a cover 4. In this embodiment, the cover 4 can be slid between a position of opening the atomization part 8 and a position of closing the atomization part 8 in a longitudinal (vertical) direction of the mist spraying device 1. The cover 4 can also serves as a power switch for the mist spraying device 1. In that case, moving the cover 4 to the position of opening the atomization part 8 activates the mist spraying device 1, and moving the cover 4 reversely to the position of closing the atomization part 8 stops the mist spraying device 1.

Figure 2:
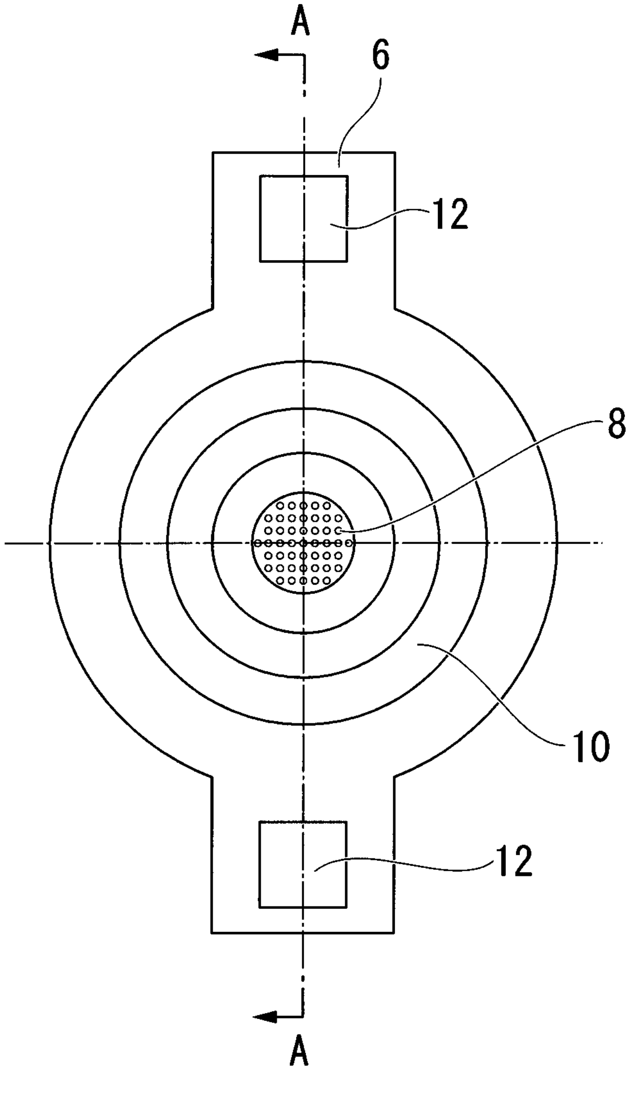
FIG. 2 is an enlarged front view of the mist generation part according to an embodiment of the present invention.
Figure 3:
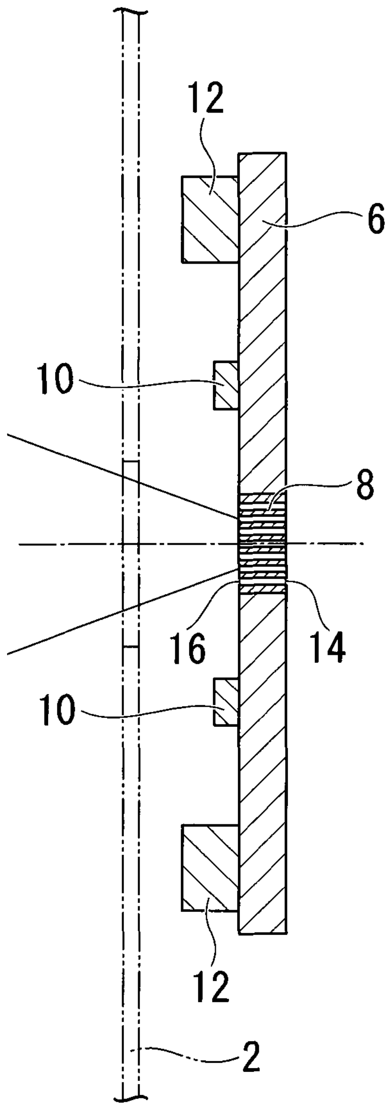
FIG. 3 is a view showing a cross-section of the mist generation part along the line A-A of FIG. 2.

FIG. 2 is a front view showing a mist generation part according to an embodiment of the present invention. FIG. 3 is a view showing a cross-section of the mist generation part according to the embodiment of the present invention along the line A-A of FIG. 2. The mist generation part includes the vibration plate 6 in which the atomization part 8 is formed, the vibration generator 10 for vibrating the vibration plate 6, and the heating element 12 for warming the atomization part 8.

In this embodiment, the vibration plate 6 is formed as a substantially circular plate. The atomization part 8 is formed at the center of the vibration plate 6. The vibration plate is preferably formed of a metal material or a plastic material such as polyimide. The plastic material is preferable because the plastic material does not result in any metal allergy. Polyimide is particularly preferable because polyimide is resistant to alcohols and preservatives which are commonly contained in a cosmetic liquid.

Figure 4A:
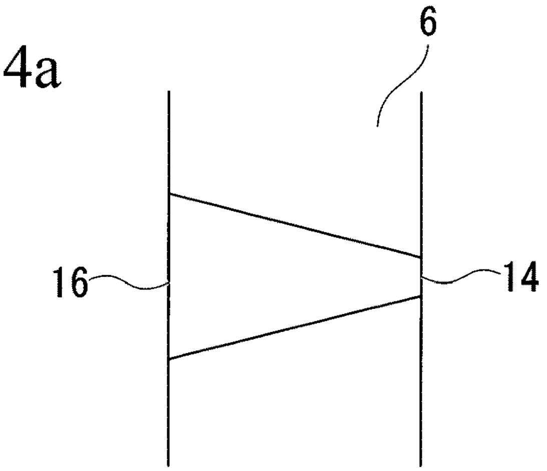
Figure 4B:
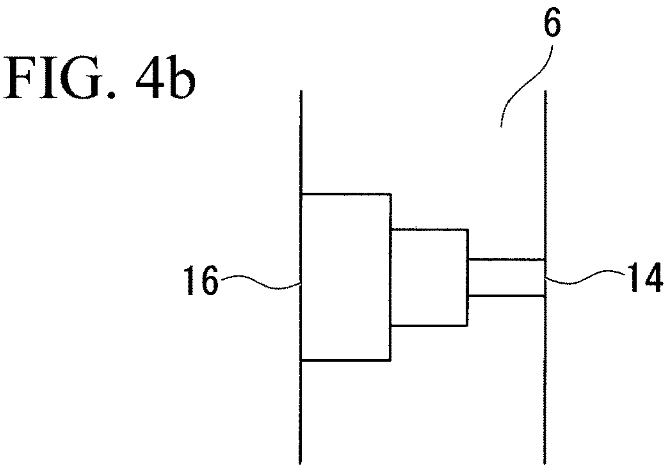
Figure 4C:
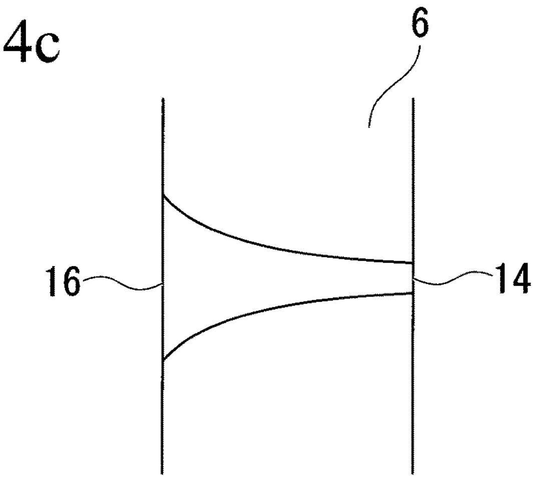

The atomization part 8 is formed of multiple micropores penetrating the vibration plate 6. Each micropore has a diameter in the order of micrometers. Each micropore has preferably a tapered cross-section in the axial direction with the diameter on a mist jetting side 16 being larger than the diameter on a liquid supply side 14 (FIG. 4*a*). This axial cross-section may also be stepped (FIG. 4*b*) or exponentially curved (FIG. 4*c*). In this embodiment, the atomization part 8 is formed in a substantially circular shape concentric with the vibration plate 6.

In this embodiment, the vibration generator 10 is formed in a substantially annular shape, and is mounted on the vibration plate 6 concentrically with the vibration plate 6 and the atomization part 8. Upon receiving power supply from the power source in the housing 2, the vibration generator 10 vibrates the vibration plate 6 in the plate thickness direction. This action causes the cosmetic liquid supplied to the liquid supply side 14 of the atomization part 8 to be atomized and sprayed from the mist jetting side 16. In this embodiment, a piezoelectric element is adopted as the vibration generator 10, although the present invention is not limited to this example.

In this embodiment, the vibration plate 6 is further provided with two heating elements 12 for warming the atomization part 8 of the vibration plate 6. In this embodiment, the two heating elements 12 are arranged at positions opposite to each other with respect to the center of the atomization part 8. In this embodiment, a Peltier element is adopted as the heating element 12, and the Peltier element is mounted such that the heat generation side of the element is in contact with the vibration plate 6.

While in this embodiment the two heating elements 12 are arranged at positions opposite to each other with respect to the center of the atomization part 8, it is also possible to arrange multiple heating elements radially around the atomization part 8. In addition, it is also possible to form the heating element 12 in an annular shape similarly to the vibration generator 10, and arrange the annular heating element 12 concentrically with the atomization part 8 and the vibration generator 10. Moreover, it is also possible to adopt an electric heating element such as a thermoelectric element as the heating element 12.

Next, the operation of the mist spraying device 1 according to this embodiment will be described. In the state where the mist spraying device 1 is not used, its cover 4 is at the position of closing the atomization part 8. To use the device, a user opens the atomization part 8 by sliding the cover 4.

When the atomization part 8 is opened, the cosmetic liquid is supplied to the liquid supply side 14 of the atomization part 8 by the supply part. At the same time, electric power can be supplied to the vibration generator 10, and the vibration generator 10 vibrates the vibration plate 6. The cosmetic liquid having been supplied is atomized by vibration of the vibration plate 6 and is sprayed from the mist jetting side 16.

Meanwhile, when the atomization part 8 is opened, electric power can also be supplied to the heating element 12. The heating element 12 supplied with the electric power warms the atomization part 8 through the vibration plate 6. Thus, even when there is clogging attributable to an increase in viscosity due to drying of the cosmetic liquid remaining in the atomization part 8, warming by the heating element 12 decreases the viscosity of the cosmetic liquid and the clogging is resolved. The mist spraying devise is advantageously used for spraying a cosmetic liquid which has a higher viscosity as compared to water and/or comprises an ingredient resulting in clogging due to drying. Such an ingredient includes a moisturizing agent, for example glycerin.

Moreover, as the heating element 12 warms the vibration plate 6, the vibration plate 6 undergoes thermal expansion. Accordingly, the micropores formed in the atomization part 8 are expanded, and the particle size of the mist to be sprayed is enlarged. Therefore, it is possible to control the diameter of the micropores by appropriately controlling the temperature of the heating element 12, and thereby to control the particle size of the mist to be sprayed.

In one embodiment, the micropores formed in the atomization part 8 preferably have a tapered cross-section, a stepped cross-section, or an exponentially curved cross-section in an axial direction with the diameter on a mist jetting side being larger than the diameter on a liquid supply side. The micropores having these cross-sectional structures can prevent variation in particle size of the mist, thereby making the particle size of the mist stable.

The present invention makes it possible to easily resolve clogging in a mist spraying device attributable to an increase in the viscosity of cosmetic liquid as it dries. In addition, it is possible to easily control the mist particle size of the cosmetic liquid to be sprayed.

EXPLANATION OF REFERENCE

1 . . . Mist spraying device
2 . . . Housing
4 . . . Cover
6 . . . Vibration plate
8 . . . Atomization part
10 . . . Vibration generator
12 . . . Heating element
14 . . . Liquid supply side
16 . . . Mist jetting side

The invention claimed is:

1. A misting device for atomizing and/or spraying a liquid, the misting device comprising:

a vibration plate comprising an atomization element;

a vibration generating element configured to vibrate the vibration plate; and a cover, wherein the cover can slide between a position of opening the atomization element and a position of closing the atomization element, wherein the atomization element comprises multiple micropores, wherein the liquid is supplied to the atomization element and atomized by vibration of the vibration plate, wherein the misting device comprises a heating element for warming the atomization element and controlling mist particle size of the liquid, and wherein moving the cover to the open position activates the misting device and moving the cover to the closed position stops the misting device.

2. The device according to claim 1, wherein the vibration generating element is configured annularly around the atomization element.

3. The device according to claim 1, wherein the heating element is configured annularly around the atomization element.

4. The device according to claim 1, wherein the vibration generating element comprises a piezoelectric element which generates vibration according to an input power.

5. The device according to claim 1, wherein the heating element comprises a Peltier element.

6. The device according to claim 1, wherein the micropores of the atomization element comprise a tapered cross-section in an axial direction, and the diameter of the micropores on a mist jetting side of the vibration plate is larger than the diameter of the micropores on a liquid supply side of the vibration plate.

7. The device according to claim 1, wherein the micropores have a stepped cross-section in the axial direction, and the diameter on the mist jetting side of the vibration plate is larger than the diameter on the liquid supply side of the vibration plate.

8. The device according to claim 1, wherein the micropores have an exponentially curved cross-section in the axial direction, and the diameter on the mist jetting side of the vibration plate is larger than the diameter on the liquid supply side of the vibration plate.

9. The device according to claim 1, wherein the liquid is a cosmetic liquid.

10. A cosmetic kit comprising:

(i) a misting device for atomizing and/or spraying a liquid, the misting device comprising:

a vibration plate comprising an atomization element;

a vibration generating element configured to vibrate the vibration plate; and a cover, wherein the cover can slide between a position of opening the atomization element and a position of closing the atomization element, wherein the atomization element comprises multiple micropores, wherein the liquid is supplied to the atomization element and atomized by vibration of the vibration plate and sprayed, wherein the misting device comprises a heating element for warming the atomization element and controlling the mist particle size of the liquid, and wherein moving the cover to the open position activates the misting device and moving the cover to the closed position stops the misting device; and (ii) a cosmetic liquid.

11. The cosmetic kit according to claim 10, wherein the device further comprises a tank, wherein the tank comprises the cosmetic liquid.

12. The cosmetic kit according to claim 10, wherein the device further comprises a package, wherein the package comprises the cosmetic liquid, and wherein the package is mountable to the device.

13. The device according to claim 9, wherein the viscosity of the cosmetic liquid is greater than the viscosity of water.

14. The device according to claim 9, wherein the cosmetic liquid comprises a moisturizing agent.

* * * * *